United States Patent [19]

Mijs et al.

[11] 4,284,769
[45] Aug. 18, 1981

[54] PREPARATION OF TRIAZINYL NITRILES

[75] Inventors: Willem J. Mijs, Rozendaal; Charles H. V. Dusseau, Heemstede; Hermannus J. M. Sinnige, Apeldoorn, all of Netherlands

[73] Assignee: Akzona Incorporated, Asheville, N.C.

[21] Appl. No.: 62,642

[22] Filed: Aug. 1, 1979

Related U.S. Application Data

[60] Continuation of Ser. No. 918,242, Jun. 23, 1978, abandoned, which is a division of Ser. No. 749,502, Dec. 10, 1976, Pat. No. 4,124,763.

[30] Foreign Application Priority Data

Dec. 16, 1975 [NL] Netherlands ............... 7514613

[51] Int. Cl.$^3$ ............... C07D 251/42; C07D 251/48; C07D 251/24; C07D 251/38
[52] U.S. Cl. ............... 544/180; 544/205; 544/206; 544/207; 544/219; 544/211; 544/212; 544/217; 544/218; 544/194
[58] Field of Search ............... 544/219, 211, 212, 206, 544/207, 205, 214, 194, 217, 218, 180

[56] References Cited

U.S. PATENT DOCUMENTS

| | | | |
|---|---|---|---|
| 3,519,627 | 7/1970 | Coats et al. | 544/207 |
| 4,124,763 | 11/1978 | Mijs et al. | 544/207 |

FOREIGN PATENT DOCUMENTS 982471 2/1965 United Kingdom.

OTHER PUBLICATIONS

Migrdichian, "The Chemistry of Organic Cyanogen Compounds," pp. 263–271 (1947).
Mizuno et al., *Chemical Abstracts*, vol. 50, pp. 1034–1035 (1956).

*Primary Examiner*—John M. Ford
*Attorney, Agent, or Firm*—Francis W. Young; Robert F. Green

[57] ABSTRACT

Novel 1,2-diaryl-1,2-dicyano-ethane compounds having the following formula:

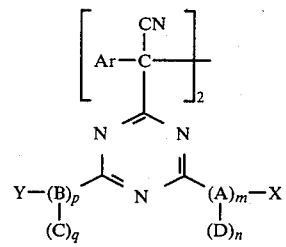

wherein
(1) m, n, p, and q independently are 0 or 1, provided that if m=0, then n=0; and if p=0, then q=0;
(2) the groups Y and C, X and D, or both, being capable of forming a heterocyclic ring having 2 to 5 carbon atoms;
(3) X, Y, C, and D are independently selected from the group consisting of substituted and unsubstituted alkyl groups having from 1 to about 20 carbon atoms, alkenyl groups having from 2 to about 20 carbon atoms, cycloalkyl groups having from 3 to 6 carbon atoms, and phenyl;
(4) if m=0, X may also be chlorine;
(5) if p=0, Y may also be chlorine;
(6) if m=1, X and D independently may also be hydrogen;
(7) if p=1, Y and C independently may also be hydrogen;
(8) if m=1 and n=1, A is nitrogen;
(9) if m=1 and n=0, A is at least one member selected from the group consisting of oxygen and sulfur;
(10) if p=1 and q=1, B is nitrogen;
(11) if p=1 and q=0, B is at least one member selected from the group consisting of oxygen and sulfur;
(12) and Ar is a substituted or unsubstituted aryl group having from 6 to 30 carbon atoms are disclosed, and a process for making the same.

3 Claims, No Drawings

PREPARATION OF TRIAZINYL NITRILES

This is a continuation of application ser. No. 918,242, filed June 23, 1978, now abandoned, which is a division of Ser. No. 749,502, filed Dec. 10, 1976, now U.S. Pat. No. 4,124,763.

BACKGROUND OF THE INVENTION

This invention relates to novel radical initiators and a process for the preparation of the same. More particularly, this invention relates to novel 1,2-diaryl-1,2-dicyano-ethane compounds and a process for preparing the same.

Processes for preparing similar compounds are described in U.S. Pat. No. 3,726,837 in which 1,2-diaryl-1,2-dicyanoethane compounds are prepared which have in the 1- and in the 2-position an aryl group, a carbonamide group or an esterified carboxyl group. Although the compounds described therein have favorable properties, there is still a great need for compounds which can be prepared with little difficulty and display an activity which is comparable to that of the known compounds at relatively low temperatures, while displaying virtually no activity at room temperature.

The present invention provides a process for the preparation of novel compounds having the above-mentioned favorable properties.

SUMMARY OF THE INVENTION

The present invention provides novel 1,2-diaryl-1,2-dicyano-ethane compounds having the following formula:

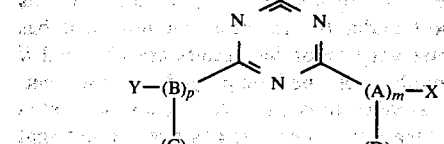

wherein (1) m, n, p, and q independently are 0 or 1, provided that if m=0, then n=0; and if p=0, then q=0;
(2) the groups Y and C, X and D, or both, being capable of forming a heterocyclic ring having 2 to 5 carbon atoms;
(3) X, Y, C, and D are independently selected from the group consisting of substituted and unsubstituted alkyl groups having from 1 to about 20 carbon atoms, alkenyl groups having from 2 to about 20 carbon atoms, cycloalkyl groups having from 3 to 6 carbon atoms, and phenyl;
(4) if m=0, X may also be chlorine;
(5) if p=0, Y may also be chlorine;
(6) if m=1, X and D independently may also be hydrogen;
(7) if p=1, Y and C independently may also be hydrogen;
(8) if m=1 and n=1, A is nitrogen;
(9) if m=1 and n=0, A is at least one member selected from the group consisting of oxygen and sulfur;
(10) if p=1 and q=1, B is nitrogen;
(11) if p=1 and q=0, B is at least one member selected from the group consisting of oxygen and sulfur;
(12) and Ar is a substituted or unsubstituted aryl group having from 6 to 30 carbon atoms.

The foregoing compounds may be prepared by a process which comprises reacting in an organic solvent a compound of the formula:

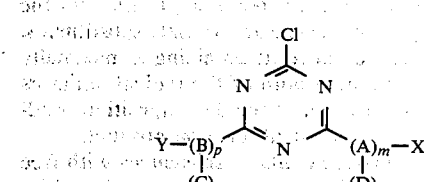

wherein the terms, A, B, C, D, X, Y, m, n, p, and q have the abovedefined meanings, and provided that neither X nor Y is a phenyl group which is linked to the triazine ring through an oxygen or sulfur atom, with the reaction product of either sodium hydride or a metal alcoholate having not more than 18 carbon atoms and a compound having the formula Ar—CH₂—CN, wherein Ar has the above-defined meaning to produce the compound:

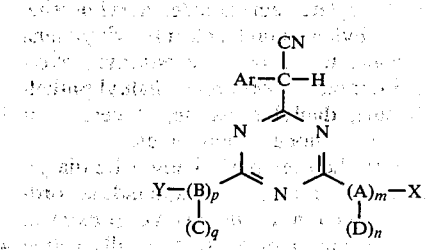

wherein the terms have the above-defined meanings. The resultant compound is then acidified, isolated, if desired, subjected to any well-known oxidative coupling reaction, and subsequently isolated.

DESCRIPTION OF THE PREFERRED EMBODIMENTS

As indicated above, the aryl groups in the present invention may be substituted or unsubstituted. Although in principle all available hydrogen atoms in the aryl groups may be replaced with other groups, it is preferable to use an unsubstituted phenyl group or a mono- or disubstituted aryl group, especially an ortho- and/or para-substituted group. Compounds substituted in the para-position are less sensitive to radical reactions in said position as a result of a steric hindrance and are relatively easy to prepare. Examples of especially suitable substituents in the aryl groups are alkyl groups having 1 to 4 carbon atoms, aryl groups, fluorine, chlorine, bromine and iodine atoms, acyl groups, aroyl groups, esterified or unesterified carboxyl groups, alkoxy groups, aryloxy groups, amino groups, in which the hydrogen atoms are substituted or not with other groups, nitro groups, alkyl or aryl sulfonyl groups or alkyl or aryl sulfinyl groups.

Suitable substituents in the X, Y, C and D groups in the formula of FIG. 2 on the formula sheet are all those groups that have no unfavorable influence on the formation of radicals or on the properties of the chemical products in the radical reactions. Suitable substituents are, for example, fluorine, chlorine, bromine or iodine, alkyl, aryl, alkoxy, alkylthio, carboxyl ester and cyano groups. Functional groups, such as hydroxyl, —NH$_2$ and/or —COOH, may also be present, so that the respective groups or radical initiator or decomposition products thereof can also be incorporated into the chemical product formed. Even an —SO$_3$H group may be present, so that the radical initiator can be emulsified in the reaction mixture to be initiated. One skilled in the art can easily choose for each special application for the most favorable groups and the appropriate substituents. It will, in general, be aimed at obtaining a maximally homogeneous distribution both of the radical initiators in the reaction mixture and of the decomposition products of the initiator in the final reaction product.

If the reaction mixture contains substances with free hydroxyl groups or amino groups, the groups X and/or Y may be chlorine. Under properly chosen reaction conditions that radical initiator will be chemically bound to one or more of the components of the reaction mixture to be initiated. It is also possible to make use of ethylenically unsaturated groups in X or Y which can also be chemically bound to the reaction product under the influence or the radicals formed in the reaction. This is especially of importance if the present radical initiators are used for the polymerization of ethylenically unsaturated monomers, such as styrene, α-methyl styrene, methyl methacrylate, acrylamide, acrylonitrile, methacrylonitrile, ethylene vinyl chloride, vinylidene chloride, vinyl acetate, divinyl benzene, N-vinyl pyrrolidone, butadiene, isoprene, chloroprene, dialkyl phthalate, diallyl carbonate, diallyl fumarate, et cetera, or mixtures of the aforementioned compounds.

As is the case with the previously known 1,2-diaryl-1,2-dicyano-ethane compounds, the compounds according to the present invention are insensitive to oxygen. Although the present compounds are generally active at a lower temperature than the known 1,2-diaryl-1,2-dicyano-ethane compounds, the present compounds can also be kept in a reaction mixture at room temperature without premature reaction taking place. The reaction can be made to start at any moment by heating the mixture. This feature may be taken advantage of in polymerization processes and in the paint and lacquers industry. Particularly attractive fields of application are the preparation of high-polymers and unsaturated polyester resins.

Compositions of the present radical initiators and polymerizable compounds, such as monomers, prepolymers, or polymers which still contain unsaturated compounds or functionl groups which react with functional groups in the radical initiators, can be given a particular desired form and be cured by heating. Curing is used as meaning polymerizatiion in a broad sense, i.e., not necessarily attended with the formation of cross-links.

Giving the compositions of radical initiators a particular form may consist in, for example, applying them as coatings, pouring them into molds, applying the compositions to glass fiber structures, impregnating all kinds of materials, injection molding, extrusion, film casting, vacuum forming, or some other forming technique. For instance, a monomer may be mixed with the radical initiators according to the invention and polymerization may be started by heating. The polymerization process may be interrupted by decreasing the temperature. At such a stage one has a mixture of monomer and polymer (also referred to herein as a prepolymer), which can be further polymerized after it has been given a particular form. If desired, cross-linking agents may, of course, be added prior to further polymerization.

The polymerization reactions with the novel radical initiators according to the invention can be carried out by using any known technique. For instance, the monomer, or the monomer mixture, can be made to polymerize as such. The polymerization also may be made to take place in a solution, a suspension, or an emulsion.

Those skilled in the art are well versed in such techniques. If desired, various additives may also be used. The radical initiators are employed in units of, for instance, 0.01 to 5% by weight, calculated on the amount of compounds to be reacted. The reaction temperature is generally in the range of 40° to 200° C.

With respect to the process for making the present initiators, in one embodiment of the present invention the radical initiators are prepared in the monomer known to be used for making corresponding compounds.

The oxidative coupling reaction utilized in the present process is well-known. Such a reaction may be carried out using an oxidizing agent such as manganese dioxide, lead dioxide, potassium permangante, potassium ferricyanide, hydrogen peroxide, nitric acid, iodine, organic peroxides such as di-tert-butyl peroxide, or by electrochemical oxidation.

In practice it is often preferred that use should be made of silver oxide or oxygen in combination with a copper amine catalyst. A large number of copper amine catalysts are described in the British Pat. No. 982,471. The temperature used is generally in the range of −40° to +130° C. and is dependent on the type of compound.

Although in the preparation of the novel radical initiator according to the present invention the reaction with the reaction product of sodium hydride may be carried out with one of a great many organic solvents which are inert under the reaction conditions, it has been found that very favorable results are obtained if dioxane or dimethoxyethane is employed as the solvent. When a metal alcoholate is used, the organic solvent is preferably benzene or toluene. It has been found that the best results are obtained if as metal alcoholate there is used a sodium alcoholate having a lower alcoholate group, such as sodium methylate.

In the case where A and B respectively represent sulfur or oxygen and X and Y respectively represent a substituted or an unsubstituted phenyl group, it is preferred to use a somewhat modified method of preparation. Such a method, can, of course, also be used if X and/or Y does not have the meaning of a phenyl group, but has one of the other meanings indicated above.

In the modified process, the reaction product of sodium hydride or a metal alcoholate and a compound of the formula Ar—CH$_2$—CN, which is utilized in the basic process, is replaced with the reaction product of an alkali solution in dimethylsulfoxide (DMSO) and a compound of the formula Ar—CH$_2$—CN. The remainder of the basic process is unchanged. It has been found that very favorable results are obtained if as organic solvent dioxan or dimethoxyethane is used.

In an alternative process for preparing the present initiators, a solution of a compound of the formula

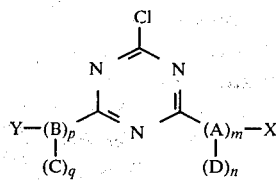

wherein the terms are as above-defined, a compound of the formula Ar—CH$_2$—CN, wherein Ar has the above-defined meaning, and an organic quaternary ammonium compound in a water-immiscible or practically water-immiscible organic solution are intimately contacted with a solution of alkali in water. After completion of the reaction, the reaction mixture is acidified and the isolated organic phase washed until neutral. The resultant monomeric product is then isolated, if desired, subjected to any known oxidative coupling reaction, and the desired product is isolated.

The amount of solution of alkali in water which is utilized may vary between wide limits. Use is often made of a concentrated alkali solution of, for example, 50% by weight NaOH in water. The alkyl groups in the tetraalkyl ammonium salt used may be straight- or branch-chained; they generally contain 1 to 20 carbon atoms. An example of a suitable tetraalkyl ammonium salt is the tetra-n-butyl ammonium salt.

Very good results were obtained with the triethyl benzyl ammonium salt. Use may be made of various organic solvents, which are not, or hardly, miscible with water and are inert to the reaction components used. It has been found that use may be made of halogenated organic solvents, and more particularly of methylene chloride. Especially with the use of the triethyl benzyl ammonium salt, these solvents may lead to very high yields. Other solvents which also give favorable results include carbon tetrachloride, 1,1,1-trichloroethane and tri- and perchloroethylene.

For the acidification in either of the two abovementioned methods of preparation, favorable results are obtained with the use of acetic acid or an inorganic acid such as hydrochloric acid.

The invention will be further described in the following examples which are of course given by way of illustration only and should not be interpreted as limitative of the present invention.

EXAMPLE I

Preparation of α,α'-bis(p-methylphenyl) α,α'-bis(2,4-dimethoxy-1,3,5-triazine)succino-nitrile 148 g. (0.8 moles) of cyanuric chloride at 30° C. were added to a suspension of 134 g. (1.6 moles) of sodium bicarbonate in a mixture of 400 ml. of methanol and 40 ml. of water. After reaction for seven hours the reaction mixture was extracted with methylene chloride, followed by washing with water until neutral, drying with MgSO$_4$ and evaporating the solvent. After recrystallization from petroleum ether (boiling point 40° to 60° C.) 126 g. of 2,4-dimethoxy-6-chloro-1,3,5-triazine were obtained with a melting point between 74.2° and 76.2° C.

Subsequently, a suspension was prepared of 1.2 g. (0.05 mol) of sodium hydroxide in 20 ml. of dimethoxyethane. To this suspension were added, with stirring, 3.28 g. (0.025 mole) of p-xylylcyanide in 20 ml. of dimethoxyethane. After 15 minutes 4.4 g. (0.25 mole) of 2,4-dimethoxy-6-chloro-1,3,5-triazine in 10 ml. of dioxane were added dropwise to the reaction mixture. After 16 hours of stirring, the reaction mixture was poured into ice water, acidified with acetic acid, and extracted with chloroform. The extract was successively washed with water, saturated sodium carbonate solution and water, until neutral, dried with magnesium sulfate and the solvent evaporated.

Next, the residue was dissolved in methanol and shaken with oxygen in the presence of Cu$_2$Cl$_2$/N,N,N,N-tetramethyl ethylene diamine as catalyst. When no more oxygen was taken up, the reaction mixture was poured into a 1% by weight solution of HCl in water and extracted with methylene chloride. The extract was washed with water until neutral, dried with magnesium sulfate, and the solvent evaporated. Recrystallization from methanol gave 2.8 g. of α,α,'-bis-(p-methylphenyl) α,α'-bis(2,4-dimethoxy-1,3,5-triazine) succinonitrile in 21% yield. The melting point of the compound was in the range of 220° to 221.7° C.

EXAMPLE II

Preparation of α,α'-bis(p-methylphenyl)α,α'-bis(2,4-dimethoxy-1,3,5-triazine)succinonitrile The 2,4-dimethoxy-6-chloro-1,3,5-triazine was prepared in the same manner as described in Example I. Subsequently, a solution was prepared of 3.6 g. (0.028 mole) of p-xylyl cyanide, 3 ml. of 50% by weight NaOH in water and 20 ml. of DMSO. A solution of 4.7 g (0.027 mole) of 2,4-dimethoxy-6-chloro-1,3,5-triazine in 15 ml. of dioxane was added dropwise over a period of 15 minutes. After one hour stirring the reaction mixture was poured into water, acidified with hydrochloric acid and extracted with methylene chloride. The extract was washed with water until neutral and dried with magnesium sulfate. The residue was subsequently treated in the same manner as described in Example I. Recrystallization from methanol gave 3.72 g. of α,α'-bis(p-methylphenyl)α,α'-bis(2,4-dimethoxy-1,3,5-triazine)succinonitrile in 25.8% yield. The melting point was the same as mentioned in Example I.

EXAMPLE III

Preparation of α,α'-bis(p-methylphenyl)α,α'-bis(2,4-dimethylthio-1,3,5-triazine)succinonitrile 20 ml. of water at −5° C. were added to a suspension of 14.7 g. (0.175 mole) of sodium bicarbonate in a solution of 15.8 g. (0.086 mole) of cyanuric chloride in 70 ml. of acetone. At a temperature of 0° C. 8.4 g. (0.175 mole) of methyl mercaptan were added to the suspension. The reaction time was nine hours and the temperature rose to 20° C. After being poured into water, the reaction mixture was extracted with ether. Following washing with water, drying with Na$_2$SO$_4$ and evaporating the solvent, the crude product was purified by recrystallization from petroleum ether (boiling point 40°-60° C.). In this way 12.2 g. of 2,4-dimethylthio-6-chloro-1,3,5-triazine were obtained in 69% yield. The melting point was in the range of 83.6° to 84.4° C.

Of the product thus prepared, 2 g. (0.0096 mole) were, as indicated in Example I for 2,4-dimethoxy-6-chloro-1,3,5-triazine, reacted with 1.27 g. (0.0096 mole) of p-xylyl cyanide and 2.5 g. (0.01 mole) of sodium hydride.

Purification and recrystallization from methanol gave 1.76 g. of (2,4-dimethylthio-s-triazinyl-6-)(tolyl-4) methyl cyanide in 60.5% yield.

The melting point was in the range of 101.2° to 102.6° C. Of the compound thus prepared 1.51 g. were dissolved in a suspension of 1.75 g. of silver oxide in 50 ml. of benzene. The resulting mixture was boiled under reflux for 60 hours, followed by adding 300 ml. of chloroform and 2 spatulas of active carbon. After another two hours boiling under reflux, the mixture was filtrated and the filtrate concentrated by evaporation. There were obtained 1.04 g. (in 68.8% yield) of white crystalline α,α'-bis(p-tolyl)α,α'-bis(2,4-dimethylthio-1,3,5-triazine)succinonitrile having a melting point of 220.8° to 221.0° C.

EXAMPLE IV

Preparation of
α,α'-bis(p-methoxyphenyl)α,α'-bis(2,4-dimethoxy-1,3,5-triazine)succinonitrile To a suspension of 2.5 g. (0.1 mole) of sodium hydride in 20 ml. of dimethoxyethane there was added a solution of 3.68 g. (0.025 mole) of p-methoxybenzyl cyanide in 30 ml. of dimethoxyethane. After 15 minutes a solution of 4.4 g. (0.025 mole) of 2,4-dimethoxy-6-chloro-1,3,5-triazine in 15 ml. of dimethoxyethane and 20 ml. of dioxane was added to the reaction mixture. Subsequently, the mixture was boiled under reflux for 60 hours, after which it was poured into a dilute (4 N) hydrochloric acid solution at 0° C. The acid solution was extracted with methylene chloride. Next, the extract was washed with a saturated sodium bicarbonate solution and with water until neutral, followed by drying with magnesium sulfate and concentrating by evaporation. The residue was isolated chromatographically on a silica gel column (silica gel 60 (70–230 mesh) ASTM; eluent:dimethoxyethane/hexane=7/3).

There were obtained 4.86 g. (in 74% yield) of 2,4-dimethoxy-s-triazinyl-6-) (anisyl-4) methyl cyanide. In the same manner as described in Example III, 2.36 g. of the compound thus prepared were dissolved in a suspension of 2.5 g. of silver oxide in 50 ml. of benzene. After 45 hours' boiling under reflux, 300 ml. of methylene chloride and two spatulas of active carbon were added. After another two hours boiling under reflux, the mixture was filtrated and concentrated by evaporation. There were obtained 1.07 g. (in 45.3% yield) of white crystalline α,α'-bis(p-methoxyphenyl)α,α'-bis(2,4-dimethoxy-1,3,5-triazine)succinonitrile having a melting point in the range of 234.0° to 234.2° C.

EXAMPLE V

Preparation of
α,α'-bis(p-tolyl)α,α'-bis(2,4-distearoxy-1,3,5-triazine)-succinonitrile 9.0 g. (0.225 mole) of powdered sodium hydroxide at a reaction temperature of 32° to 37° C. were added to a solution of 18.4 g. (0.1 mole) of cyanuric chloride and 51.2 g. (0.2 mole) of stearyl alcohol in 200 ml. of dioxane over a period of 20 minutes. After seven hours the reaction mixture was poured into 500 ml. of petroleum ether (boiling point 60° C.).

The solution thus obtained was washed with water, dried with MgSO4, and concentrated by evaporation.

10 g. (0.016 mole) of the resulting product and 3.64 g. (0.016 mole) of triethyl benzyl ammonium chloride and 2.09 g. (0.016 mole) of p-xylyl cyanide were dissolved in 400 ml. of methylene chloride. With a supertorax stirrer, the solution obtained was vigorously stirred for three hours in the presence of 50 ml. of 50% by weight-—sodium hydroxide. After completion of the reaction, the reaction mixture was poured into 400 ml. of 4 N HCl, followed by washing the isolated organic phase with water until neutral, drying with MgSO4, and concentrating by evaporation. The (2,4-distearoxy-s-triazinyl-6-) (tolyl-4)methyl cyanide was purified by recrystallization from methanol. There were obtained 11.1 g. of product in 87% yield. Starting from 3.8 g. the coupling reaction was carried out by using the same procedure as described in Example I using oxygen in the presence of Cu2Cl2/N,N,N,N-tetramethyl ethylene diamine as catalyst, with the exception that it was performed in a mixture of equal parts by volume of methanol and methylene chloride.

Recrystallization from acetone gave 3.14 g. (in 83% yield) of white crystalline α,α'-bis(p-tolyl)α,α'-bis(2,4-distearoxy-1,3,5-triazine)succinonitrile having a melting point in the range of 75.0° to 82.3° C.

EXAMPLE VI

Preparation of α,α'-bis(p-methylphenyl) α,α'-bis (2,4-dipiperidino-1,3,5-triazine)succinonitrile At a reaction temperature of 15° to 20° C. a solution of 19.0 g. (0.2 mole) of phenol and 8.0 g. (0.2 mole) of sodium hydroxide in 75 ml. of water was added dropwise to a solution of 18.4 g. (0.1 mole) of cyanuric chloride in 90 ml. of acetone.

After 4½ hours the precipitate formed was removed by suction, washed with water and dried (with MgSO4). Purification by recrystallization from n-heptane gave 24.7 g. of 2,4-diphenoxy-6-chloro-1,3,5-triazine in 82% yield. The melting point was 119°–121° C.

In the same manner as described in Example V, 3.23 g. of this product were coupled to 1.41 g. of p-xylyl cyanide by way of a phase-transfer catalyzed two-phase reaction.

Purification of the reaction product: (2,4-diphenoxy-s-triazine-6-) (tolyl-4)methyl cyanide by recrystallization from ethyl acetate gave 3.6 g. of the title product in 85% yield.

The compound (2,4-dipiperidino-s-triazinyl-6) (tolyl-4)methyl cyanide was obtained by boiling the above-mentioned reaction product with two molar equivalents of piperidine for 16 hours in chloroform under reflux. After the solvent had been evaporated, the residue was sublimated, with phenol escaping from the reaction mixture.

After the residue had been boiled in an ether/chloroform mixture, the solid matter was filtered off, dissolved in methylene chloride, and the solution washed with water. Following drying with MgSO4 the solvent was evaporated and the resulting solid matter boiled in ether. Subsequently, the solid matter was filtered off and dried. The coupling reaction was carried out in the same manner as described in Example III, using silver oxide in boiling toluene. The product was obtained in 49% yield. The melting point was in the range of 257.0° to 258.0° C.

EXAMPLE VII

Preparation of α,α'-bis(p-chorophenyl)α,α'-bis(2,4-dimethoxy-1,3,5-triazine)succinonitrile In the preparation of this compound, the same procedure was used as described in Example IV, with the exception that it was started from 3.79 g. (0.025 mole) of p-chlorobenzyl cyanide. Further, the period over which the reaction mixture was boiled under reflux was only one hour instead of 60 hours. Further treatment resulted in a residue which after recrystallization from a mixture of ethanol and ethyl acetate gave 5.05 g. of the title product in 74.3% yield. The melting point was in the range of 238.4° and 241.4° C.

EXAMPLES VIII–XII

In these examples the reactivities are determined of the radical initiators and polymerization initiators according to the invention and some known radical initiators. The reactivity is indicated with the polymerization constant Kp. The latter is very much dependent on the temperature and occurs in the formula $Rp = Kp (M) (I)^{\frac{1}{2}}$ where Rp is the polymerization speed, (M) the concentration of the monomer and (I) the concentration of the radical initiator (see "Die Makromolekulare Chemie" 157 (1972), p.279 ff). In all determinations 50 ml. of the monomer were mixed with the radial initiators listed in the following Table and transferred to a dilatometer. The dilatometer was cooled to −80° C., filled with nitrogen, followed by applying vacuum to it; the last two treatments were repeated three times. Then the dilatometer was placed in a thermostated bath which had been set to the polymerization temperature mentioned in the table below. The concentration values were determined in accordance with the standard dilatometric technique (see "Angewandte Chemie" 59 (1947), p90). From the values obtained the conversion and the Kp-values were successively determined. The Table below gives the values obtained for the compounds are prepared in the Examples I through VII. For comparison also the Kp-values of some known radical initiators, namely, α,α'-bis(methoxycarbo)α,α'-bis(p-methylphenyl)succinonitrile(dl) (IX), dilauroyl peroxide (X), di-t-butyl perpivalate (XI) and tert. butyl peroxypivalate (XII) are listed in the Table.

Because of the poor solubility of some of the radical initiators prepared in the preceding examples, the determination of the Kp-value was started from 0.05% by weight, whereas normally 0.2% by weight is included in the monomer to be polymerized. The Kp-values of other radical initiators in styrene are listed in the Tables 2 and 3 on page 283 of the aforementioned article in "Die Makromolekulare Chemie".

TABLE I

| radical initiator of example | Kp-value × 10⁴ | | | | |
|---|---|---|---|---|---|
| | Methylmethacrylate temperature °C. | | Styrene temperature °C. | | |
| | 50 | 60 | 70 | 80 | 90 |
| I + II | 3.85 | 7.5 | x | x | |
| III | 2.85 | 5.92 | x | x | |
| IV | 1.1 | 2.7 | x | x | |
| V | 2.32 | 4.48 | 3.05 | 7.86 | |
| VI | no polymerization | | 1.60 | 3.56 | |
| VII | 2.10 | 5.52 | 6.10 | 5.70 | |
| IX | | | 1.3 | 3.4 | |
| X | | | 2.4 | 5.8 | |
| XI | | | 4.2 | 10.1 | |
| XII | 3.0 | | | | | x: Although at these temperatures polymerization took place, the conversion-time curves were non-linear. The difference in behaviour between the compound of Example V and that of I through IV, is probably due to a far better compatibility of the compound of Example V in styrene and in polystyrene.

What is claimed is:
1. A process for the preparation of novel radical initiators comprising
   (a) contacting a solution of (i) a compound of the formula

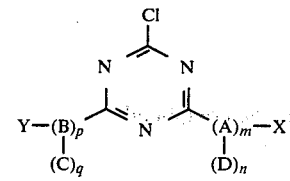

wherein
   (1) m, n, p, and q independently are 0 or 1, provided if m=0, then n=0; and if p=0, then q=0;
   (2) the groups Y, B and C, X, A and D, or both are capable of forming a hetrocyclic ring having 2 to 5 carbon atoms;
   (3) X, Y, C, and D are independently selected from the group consisting of substituted and unsubstituted alkyl groups having from 1 to about 20 carbon atoms, the substituted alkyl groups being substituted with a substituent selected from the group consisting of fluorine, chlorine, bromine, iodine, alkyl, aryl, alkoxy, alkylthio, carboxylester, cyano, hydroxyl, —NH₂, —COOH, and —SO₃H; alkenyl groups having from about 2 to about 20 carbon atoms, cycloalkyl groups having from 3 to 6 carbon atoms, and phenyl;
   (4) if m=0, X may also be chlorine;
   (5) if p=0, Y may also be chlorine;
   (6) if m=1, X and D independently may also be hydrogen;
   (7) if p=1, Y and C independently may also be hydrogen;
   (8) if m=1, and n=1, A is nitrogen;
   (9) if m=1 and n=0, A is one member selected from the group consisting of oxygen and sulfur;
   (10) if p=1 and q=1, B is nitrogen;
   (11) if p=1 and q=0, B is one member selected from the group consisting of oxygen and sulfur;
   (12) and Ar is a substituted or unsubstituted aryl group having from 6 to 30 carbon atoms, the substituted aryl group being substituted with a substituent selected from the group consisting of alkyl having 1 to 4 carbon atoms, aryl, fluorine, chlorine, bromine, iodine, acyl, aroyl, carboxyl, alkoxy, aryloxy, amino, nitro, alkyl sulfonyl, aryl sulfonyl, alkyl sulfinyl, and aryl sulfinyl, with a compound of the formula Ar—CH₂—CN, a quaternary ammonium compound in a water immiscible, or practically water-immiscible organic solvent, and a solution of alkali in water;
   (b) allowing the reaction to go to substantial completion;

(c) acidifying the reaction mixture;

(d) isolating the organic phase;

(e) washing the organic phase until neutral, to thus produce the compound

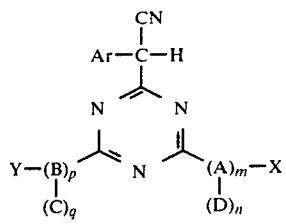

wherein the terms A, Ar, B, C, D, X, Y, m, n, p, and q have the meanings defined above;

(f) oxidatively coupling the foregoing compound; and (g) isolating the novel radical initiator.

2. The process of claim 1 wherein the organic solvent is a halogenated organic solvent.

3. The process of claim 1 wherein the organic solvent is methylene chloride and the organic quaternary ammonium compound is triethyl benzyl ammonium salt.

* * * * *